United States Patent
Prevost et al.

(10) Patent No.: US 8,029,548 B2
(45) Date of Patent: *Oct. 4, 2011

(54) FLEXIBLE SPINAL STABILIZATION ELEMENT AND SYSTEM

(75) Inventors: Julien J. Prevost, Memphis, TN (US); Dimitri K. Protopsaltis, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 653 days.

This patent is subject to a terminal disclaimer.

(21) Appl. No.: 12/114,843

(22) Filed: May 5, 2008

(65) Prior Publication Data

US 2009/0275986 A1  Nov. 5, 2009

(51) Int. Cl.
*A61B 17/70* (2006.01)
(52) U.S. Cl. ........................ 606/278; 606/264
(58) Field of Classification Search .................. 606/279, 606/254, 257, 261, 86 A, 278, 264
See application file for complete search history.

(56) References Cited

U.S. PATENT DOCUMENTS

| | | | |
|---|---|---|---|
| 4,078,559 A | 3/1978 | Nissinen |
| 4,257,409 A | 3/1981 | Bacal et al. |
| 4,269,178 A | 5/1981 | Keene |
| 4,289,123 A | 9/1981 | Dunn |
| 4,411,259 A | 10/1983 | Drummond |
| 4,693,240 A | 9/1987 | Evans |
| 4,697,582 A | 10/1987 | William |
| 4,743,260 A | 5/1988 | Burton |
| 4,779,333 A | 10/1988 | Rabe et al. |
| 4,805,602 A | 2/1989 | Puno et al. |
| 4,836,196 A | 6/1989 | Park et al. |
| 4,887,596 A | 12/1989 | Sherman |
| 4,932,975 A | 6/1990 | Main et al. |
| 4,969,886 A | 11/1990 | Cziffer et al. |
| 5,002,576 A | 3/1991 | Fuhrmann et al. |
| 5,030,220 A | 7/1991 | Howland |
| 5,067,955 A | 11/1991 | Cotrel |
| 5,092,866 A | 3/1992 | Breard et al. |
| 5,152,303 A | 10/1992 | Allen |
| 5,176,680 A | 1/1993 | Vignaud et al. |
| 5,180,393 A | 1/1993 | Commarmond |
| 5,257,993 A | 11/1993 | Asher et al. |
| 5,306,275 A | 4/1994 | Bryan |
| 5,312,405 A | 5/1994 | Korotko et al. |
| 5,375,823 A | 12/1994 | Navas |

(Continued)

FOREIGN PATENT DOCUMENTS

EP    0612507 A1    8/1994

(Continued)

OTHER PUBLICATIONS

Office Action mailed Mar. 3, 2011. U.S. Appl. No. 12/120,573. (Double patenting rejection).

*Primary Examiner* — Pedro Philogene

(57) ABSTRACT

Systems and devices for providing dynamic stabilization of one or more spinal motion segments are provided. The systems include a connecting element between two or more bone anchor assemblies that can be attached to two or more vertebral bodies of at least one spinal motion segment. The connecting element includes a first end, a second end, an intermediate resilient element and a sheathed tether extending from the first end to the second end and through the resilient intermediate element.

20 Claims, 5 Drawing Sheets

U.S. PATENT DOCUMENTS

| | | | |
|---|---|---|---|
| 5,409,488 A | 4/1995 | Ulrich | |
| 5,413,576 A | 5/1995 | Rivard | |
| 5,415,661 A | 5/1995 | Holmes | |
| 5,423,816 A | 6/1995 | Lin | |
| 5,437,671 A | 8/1995 | Lozier et al. | |
| 5,443,467 A | 8/1995 | Biedermann et al. | |
| 5,480,401 A | 1/1996 | Navas | |
| 5,486,174 A | 1/1996 | Fournet-Fayard et al. | |
| 5,496,321 A | 3/1996 | Puno et al. | |
| 5,520,689 A | 5/1996 | Schlapfer et al. | |
| 5,540,688 A | 7/1996 | Navas | |
| 5,562,660 A | 10/1996 | Grob | |
| 5,562,737 A | 10/1996 | Graf | |
| 5,584,834 A | 12/1996 | Errico et al. | |
| 5,649,926 A | 7/1997 | Howland | |
| 5,651,789 A | 7/1997 | Cotrel | |
| 5,672,175 A | 9/1997 | Martin | |
| 5,683,390 A | 11/1997 | Metz-Stavenhagen et al. | |
| 5,697,977 A | 12/1997 | Pisharodi | |
| 5,702,395 A | 12/1997 | Hopf | |
| 5,704,936 A | 1/1998 | Mazel | |
| 5,716,356 A | 2/1998 | Biedermann et al. | |
| 5,733,284 A | 3/1998 | Martin | |
| 5,810,817 A | 9/1998 | Roussouly et al. | |
| 5,910,141 A | 6/1999 | Morrison et al. | |
| 5,910,142 A | 6/1999 | Tatar | |
| 5,928,284 A | 7/1999 | Mehdizadeh | |
| 5,938,662 A | 8/1999 | Rinner | |
| 5,938,663 A | 8/1999 | Petreto | |
| 5,961,516 A | 10/1999 | Graf | |
| 5,993,448 A | 11/1999 | Remmler | |
| 6,015,409 A | 1/2000 | Jackson | |
| 6,063,090 A | 5/2000 | Schlapfer | |
| 6,086,588 A | 7/2000 | Ameil et al. | |
| 6,090,111 A | 7/2000 | Nichols | |
| 6,123,707 A | 9/2000 | Wagner | |
| 6,132,430 A | 10/2000 | Wagner | |
| 6,159,212 A | 12/2000 | Schoedinger, III et al. | |
| 6,221,077 B1 | 4/2001 | Rinner et al. | |
| 6,241,730 B1 | 6/2001 | Alby | |
| 6,248,106 B1 | 6/2001 | Ferree | |
| 6,267,764 B1 | 7/2001 | Elberg | |
| 6,290,700 B1 | 9/2001 | Schmotzer | |
| 6,296,643 B1 | 10/2001 | Hopf et al. | |
| 6,299,616 B1 | 10/2001 | Beger | |
| 6,355,039 B1 | 3/2002 | Troussel et al. | |
| 6,355,040 B1 | 3/2002 | Richelsoph et al. | |
| 6,368,320 B1 | 4/2002 | Le Couedic et al. | |
| 6,402,750 B1 | 6/2002 | Atkinson et al. | |
| 6,423,065 B2 | 7/2002 | Ferree | |
| 6,440,133 B1 | 8/2002 | Beale et al. | |
| 6,440,169 B1 | 8/2002 | Elberg et al. | |
| 6,554,831 B1 | 4/2003 | Rivard et al. | |
| 6,582,468 B1 | 6/2003 | Gauchet | |
| 6,613,050 B1 | 9/2003 | Wagner et al. | |
| 6,616,669 B2 | 9/2003 | Ogilvie et al. | |
| 6,626,904 B1 | 9/2003 | Jammet et al. | |
| 6,626,906 B1 | 9/2003 | Young | |
| 6,645,207 B2 | 11/2003 | Dixon et al. | |
| 6,706,044 B2 | 3/2004 | Kuslich et al. | |
| 6,709,434 B1 | 3/2004 | Gournay et al. | |
| 6,736,818 B2 | 5/2004 | Perren et al. | |
| 6,783,527 B2 | 8/2004 | Drewry et al. | |
| 6,793,657 B2 | 9/2004 | Lee et al. | |
| 6,835,205 B2 | 12/2004 | Atkinson et al. | |
| 6,890,333 B2 | 5/2005 | von Hoffmann et al. | |
| 6,932,822 B2 | 8/2005 | Oribe et al. | |
| 6,966,910 B2 | 11/2005 | Ritland | |
| 6,986,771 B2 | 1/2006 | Paul et al. | |
| 6,989,011 B2 | 1/2006 | Paul et al. | |
| 6,991,632 B2 | 1/2006 | Ritland | |
| 7,011,659 B2 | 3/2006 | Lewis et al. | |
| 7,018,379 B2 | 3/2006 | Drewry et al. | |
| 7,029,475 B2 | 4/2006 | Panjabi | |
| 7,066,957 B2 | 6/2006 | Graf | |
| 7,083,621 B2 | 8/2006 | Shaolian et al. | |
| 7,083,622 B2 | 8/2006 | Simonson | |
| 7,104,992 B2 | 9/2006 | Bailey | |
| 7,125,410 B2 | 10/2006 | Freudiger | |
| 7,704,271 B2 | 4/2010 | Abdou | |
| 7,785,350 B2 * | 8/2010 | Eckhardt et al. | 606/254 |
| 7,815,664 B2 * | 10/2010 | Sherman et al. | 606/257 |
| 2002/0133155 A1 | 9/2002 | Ferree | |
| 2002/0151900 A1 | 10/2002 | Glascott | |
| 2002/0161368 A1 | 10/2002 | Foley et al. | |
| 2003/0060824 A1 | 3/2003 | Viart et al. | |
| 2003/0083657 A1 | 5/2003 | Drewry et al. | |
| 2003/0100904 A1 | 5/2003 | Biedermann | |
| 2003/0114853 A1 | 6/2003 | Burgess et al. | |
| 2003/0171749 A1 | 9/2003 | Le Couedic et al. | |
| 2003/0191470 A1 | 10/2003 | Ritland | |
| 2003/0204260 A1 | 10/2003 | Ferree | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0015166 A1 | 1/2004 | Gorek | |
| 2004/0049189 A1 | 3/2004 | Le Couedic et al. | |
| 2004/0049190 A1 | 3/2004 | Biedermann et al. | |
| 2004/0102781 A1 | 5/2004 | Jeon | |
| 2004/0143264 A1 | 7/2004 | McAfee | |
| 2004/0147928 A1 | 7/2004 | Landry et al. | |
| 2004/0172024 A1 | 9/2004 | Gorek | |
| 2004/0172025 A1 | 9/2004 | Drewry et al. | |
| 2004/0186474 A1 | 9/2004 | Matthis et al. | |
| 2004/0215191 A1 | 10/2004 | Kitchen | |
| 2004/0225289 A1 | 11/2004 | Biedermann et al. | |
| 2004/0236327 A1 | 11/2004 | Paul et al. | |
| 2004/0236329 A1 | 11/2004 | Panjabi | |
| 2005/0033434 A1 | 2/2005 | Berry | |
| 2005/0038432 A1 | 2/2005 | Shaolian et al. | |
| 2005/0049708 A1 | 3/2005 | Atkinson et al. | |
| 2005/0056979 A1 | 3/2005 | Studer et al. | |
| 2005/0065515 A1 | 3/2005 | Jahng | |
| 2005/0065516 A1 | 3/2005 | Jahng | |
| 2005/0085813 A1 | 4/2005 | Spitler et al. | |
| 2005/0085815 A1 | 4/2005 | Harms et al. | |
| 2005/0101954 A1 | 5/2005 | Simonson | |
| 2005/0113927 A1 | 5/2005 | Malek | |
| 2005/0124991 A1 | 6/2005 | Jahng | |
| 2005/0131405 A1 | 6/2005 | Molz, IV et al. | |
| 2005/0131407 A1 | 6/2005 | Sicvol et al. | |
| 2005/0143737 A1 | 6/2005 | Pafford et al. | |
| 2005/0143823 A1 | 6/2005 | Boyd et al. | |
| 2005/0149020 A1 | 7/2005 | Jahng | |
| 2005/0149023 A1 | 7/2005 | Ritland | |
| 2005/0154390 A1 | 7/2005 | Biedermann et al. | |
| 2005/0165396 A1 | 7/2005 | Fortin et al. | |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0177164 A1 | 8/2005 | Walters et al. | |
| 2005/0182400 A1 | 8/2005 | White | |
| 2005/0182401 A1 | 8/2005 | Timm et al. | |
| 2005/0182409 A1 | 8/2005 | Callahan et al. | |
| 2005/0192574 A1 | 9/2005 | Blain | |
| 2005/0203513 A1 | 9/2005 | Jahng et al. | |
| 2005/0203514 A1 | 9/2005 | Jahng et al. | |
| 2005/0203517 A1 | 9/2005 | Jahng et al. | |
| 2005/0203518 A1 | 9/2005 | Biedermann et al. | |
| 2005/0203519 A1 | 9/2005 | Harms et al. | |
| 2005/0209698 A1 | 9/2005 | Gordon et al. | |
| 2005/0228385 A1 | 10/2005 | Iott et al. | |
| 2005/0261685 A1 | 11/2005 | Fortin et al. | |
| 2005/0261686 A1 | 11/2005 | Paul | |
| 2005/0277922 A1 | 12/2005 | Trieu et al. | |
| 2005/0277932 A1 | 12/2005 | Farris | |
| 2005/0288670 A1 | 12/2005 | Panjabi et al. | |
| 2005/0288672 A1 | 12/2005 | Ferree | |
| 2006/0009768 A1 | 1/2006 | Ritland | |
| 2006/0079892 A1 | 4/2006 | Roychowdhury et al. | |
| 2006/0079894 A1 | 4/2006 | Colleran et al. | |
| 2006/0079896 A1 | 4/2006 | Kwak et al. | |
| 2006/0084991 A1 | 4/2006 | Borgstrom et al. | |
| 2006/0084994 A1 | 4/2006 | Atkinson et al. | |
| 2006/0106380 A1 | 5/2006 | Colleran et al. | |
| 2006/0111715 A1 | 5/2006 | Jackson | |

| | | |
|---|---|---|
| 2006/0129149 A1 | 6/2006 | Iott et al. |
| 2006/0142758 A1 | 6/2006 | Petit |
| 2006/0149238 A1 | 7/2006 | Sherman et al. |
| 2006/0149242 A1 | 7/2006 | Kraus et al. |
| 2006/0195093 A1 | 8/2006 | Jahng |
| 2006/0241771 A1 | 10/2006 | Gordon et al. |
| 2006/0247625 A1 | 11/2006 | Morrison et al. |
| 2006/0247779 A1 | 11/2006 | Gordon et al. |
| 2006/0264935 A1 | 11/2006 | White |
| 2006/0264937 A1 | 11/2006 | White |
| 2006/0264942 A1 | 11/2006 | Lim et al. |
| 2007/0005063 A1 | 1/2007 | Bruneau et al. |
| 2007/0049937 A1 | 3/2007 | Matthis et al. |
| 2007/0093813 A1 | 4/2007 | Callahan, II et al. |
| 2007/0123864 A1 | 5/2007 | Walder et al. |
| 2007/0123866 A1 | 5/2007 | Gerbec et al. |
| 2007/0198014 A1 | 8/2007 | Graf et al. |
| 2007/0233075 A1 | 10/2007 | Dawson |
| 2007/0270814 A1 | 11/2007 | Lim et al. |
| 2007/0270837 A1 | 11/2007 | Eckhardt et al. |
| 2008/0183212 A1 | 7/2008 | Veldman et al. |
| 2009/0234388 A1 * | 9/2009 | Patterson et al. ............. 606/246 |
| 2009/0287252 A1 | 11/2009 | Marik et al. |
| 2011/0022092 A1 | 1/2011 | Trieu |

FOREIGN PATENT DOCUMENTS

| | | |
|---|---|---|
| EP | 0669109 A1 | 8/1995 |
| EP | 1757243 A1 | 2/2007 |
| FR | 2715825 A1 | 8/1995 |
| FR | 2743290 A1 | 7/1997 |
| FR | 2844180 A1 | 3/2004 |
| WO | 9944527 A1 | 9/1999 |
| WO | 2005039454 A2 | 5/2005 |
| WO | 2005087121 A1 | 9/2005 |

* cited by examiner

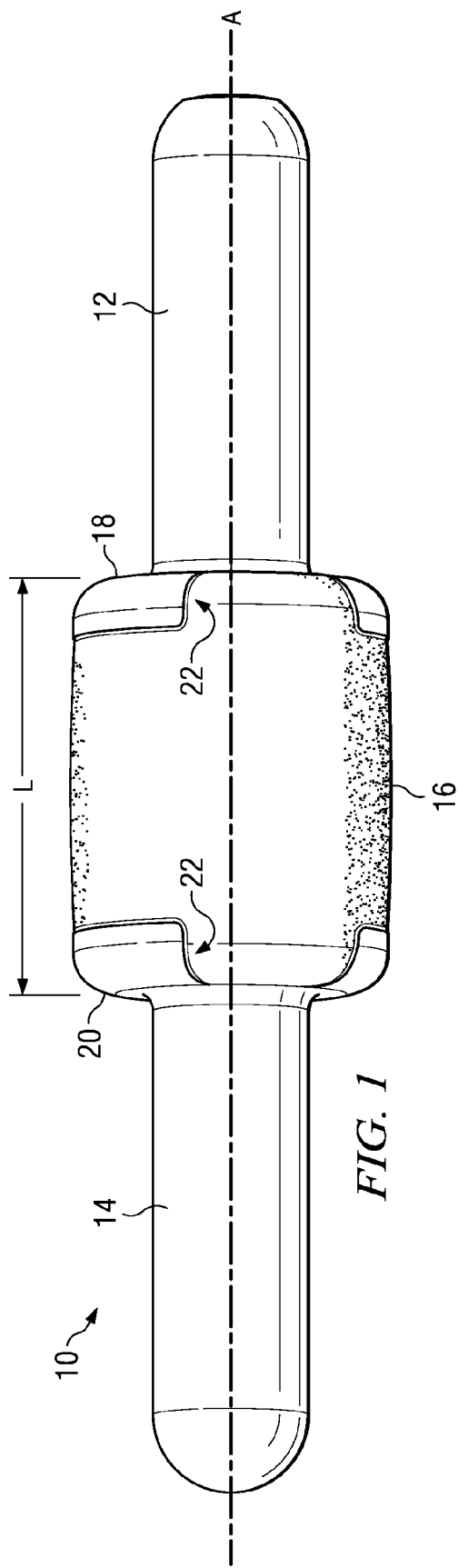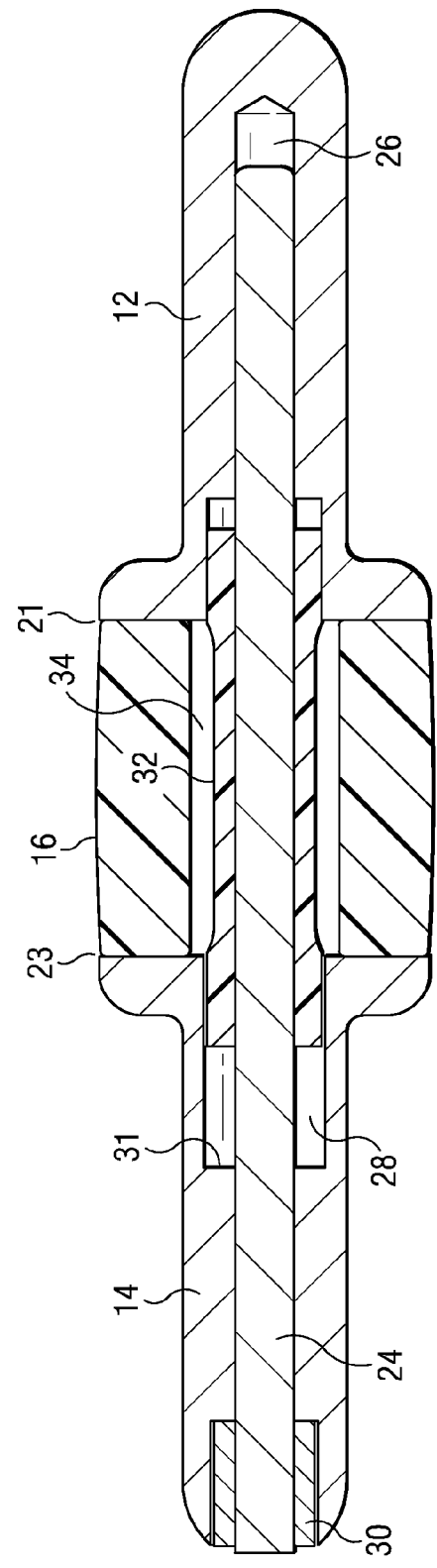
*FIG. 1*
*FIG. 2*

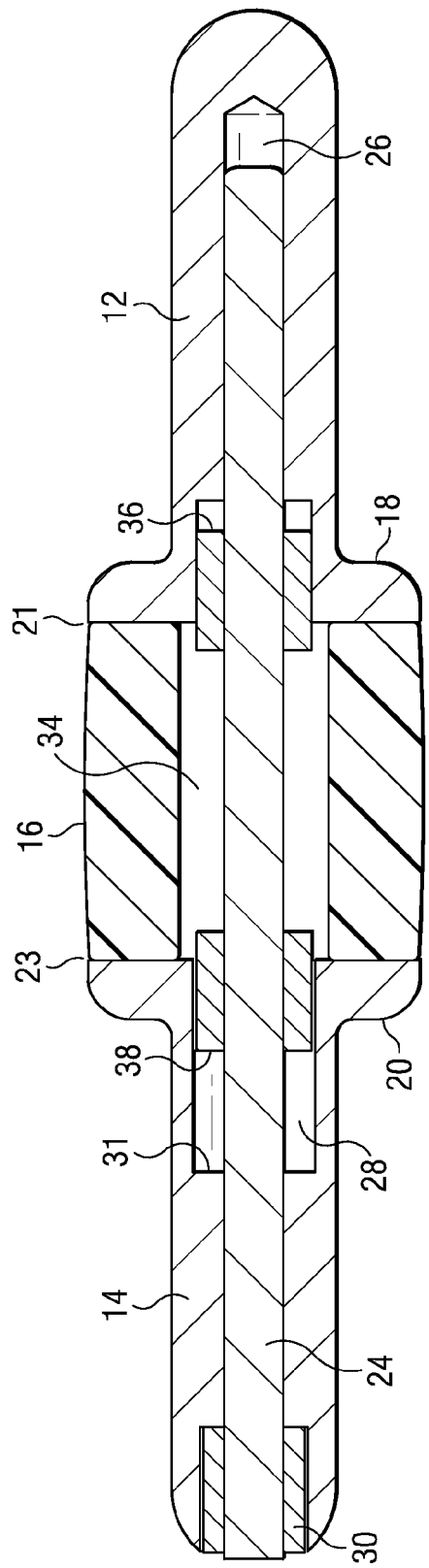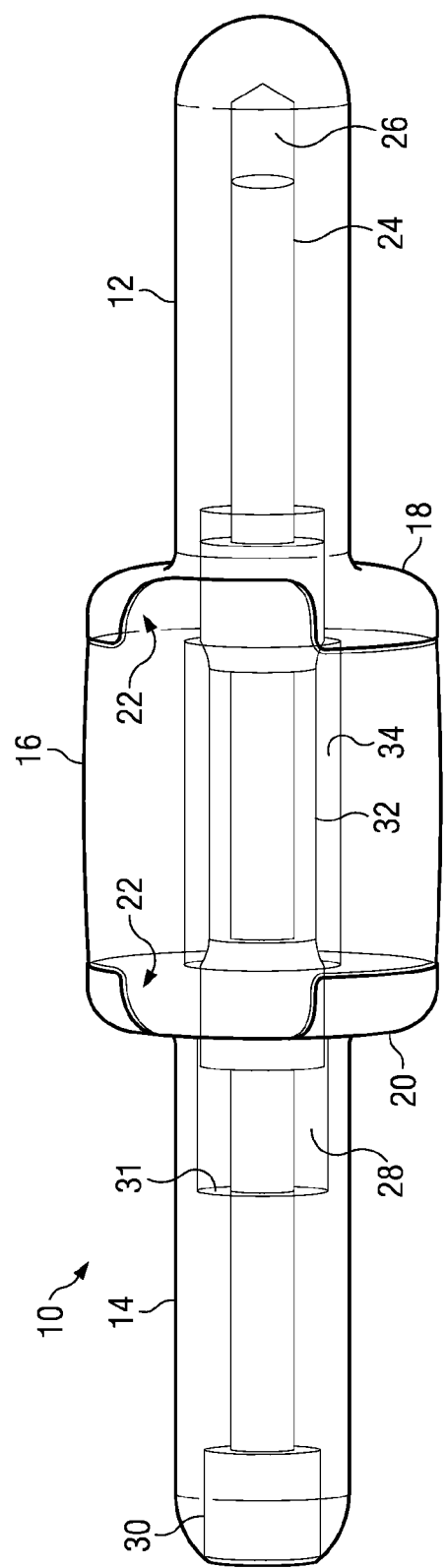

FLEXIBLE SPINAL STABILIZATION ELEMENT AND SYSTEM

CROSS-REFERENCE TO RELATED APPLICATIONS

United States patent applications "Instruments and methods for minimally invasive spinal stabilization," Ser. No. 10/769,569, filed Jan. 30, 2004; "Systems and methods for spinal stabilization with flexible elements," Ser. No. 11/028,999, filed Jan. 4, 2005; and "Instruments and methods for minimally invasive spinal stabilization," Ser. No. 11/483,299, filed Jul. 7, 2006, include related subject matter, are commonly owned, and are hereby incorporated by reference in their entireties.

BACKGROUND

The present disclosure relates to devices, systems, and methods for preserving motion between vertebrae, and more particularly, to devices, systems, and methods for improving posterior spinal function with a pedicle-based implant.

Severe back pain, limited motion, and nerve damage may be caused by injured, degraded, or diseased spinal anatomy. Affected spinal joints, and particularly discs and ligaments, can be difficult to treat externally and may necessitate surgery.

In some instances, the diseases, injuries or malformations affecting spinal motion segments are treated by fusing two adjacent vertebrae together using transplanted bone tissue, an artificial fusion component, or other compositions or devices. In some surgical treatments, posterior rods may be attached to variously affected spinal levels to inhibit or limit motion, with or without, spinal fusion. These posterior rods are frequently rigid rods which substantially, if not totally, eliminate freedom of motion for bending in flexion and extension. Other important motions may similarly be eliminated. Therefore, alternatives to substantially rigid rod systems are needed which allow for certain motion and which more closely approximate the natural function of the motion segments.

Elongated connecting elements, such as rods, plates, tethers, wires, cables, and other devices have been implanted along the spinal column and connected between two or more anchors engaged between one or more spinal motion segments. Such connecting elements can provide a rigid construct that resists movement of the spinal motion segment in response to spinal loading or movement of the spinal motion segment by the patient. Other connecting elements can resist loading or movement of the spinal motion segment that creates a tension force on the connecting element; however, the connecting element collapses in response to any compression loading and provides little or no resistance in response to such forces or movement.

SUMMARY

According to one exemplary embodiment, an elongated connecting element for stabilizing a first vertebra with respect to a second vertebra is disclosed. The elongated connecting element includes a first end member and a second end member substantially aligned along a longitudinal axis, a resilient intermediate element positioned between the first end member and the second end member and having a length L, a tether extending between the first end member and the second end member and through the resilient intermediate element, and a sheath at least partially surrounding the tether along a portion of the length of the tether. The resilient intermediate element may abut the first end member at a first abutment and the second end member at a second abutment. The sheath at least partially surrounds the tether substantially continuously along the entire length L According to another exemplary embodiment, an elongated connecting element for stabilizing a first vertebra with respect to a second vertebra is disclosed. The elongated connecting element includes a first end member and a second end member substantially aligned along a longitudinal axis, a resilient intermediate element positioned between the first end member and the second end member, and having a length L, a tether extending between the first end member and the second end member and through the resilient intermediate element, and a sheath at least partially surrounding the tether along a portion of the length of the tether. The resilient intermediate element may abut the first end member at a first abutment and the second end member at a second abutment. The sheath is discontinuous and includes at least one first collar disposed in a bore within the first end member radially inwardly from the first abutment and at least one second collar disposed in a bore within the second end member radially inwardly from the second abutment.

According to another exemplary embodiment, a spinal stabilization system is disclosed that includes at least a first bone anchor system connectable to a first vertebra and a second bone anchor system connectable to a second vertebra, as well as a flexible elongated connecting element configured to extend between the first bone anchor system and the second bone anchor system. The flexible elongated connecting element includes a sheathed tether extending through a resilient intermediate member disposed such that the resilient intermediate member is arranged between the first bone anchor system and the second bone anchor system when the flexible elongated connecting element is connected thereto.

These and other features will become apparent from the following description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

FIG. 1 is a perspective view of an exemplary embodiment of an elongated connecting element according to the present invention;

FIG. 2 is a cross-sectional view of an exemplary embodiment of an elongated connecting element according to the present invention;

FIG. 3 is a cross-sectional view of an exemplary embodiment of an elongated connecting element according to the present invention;

FIG. 4 is a phantom view of the embodiment of the elongated connecting element of FIG. 2;

DETAILED DESCRIPTION

Figure 5:
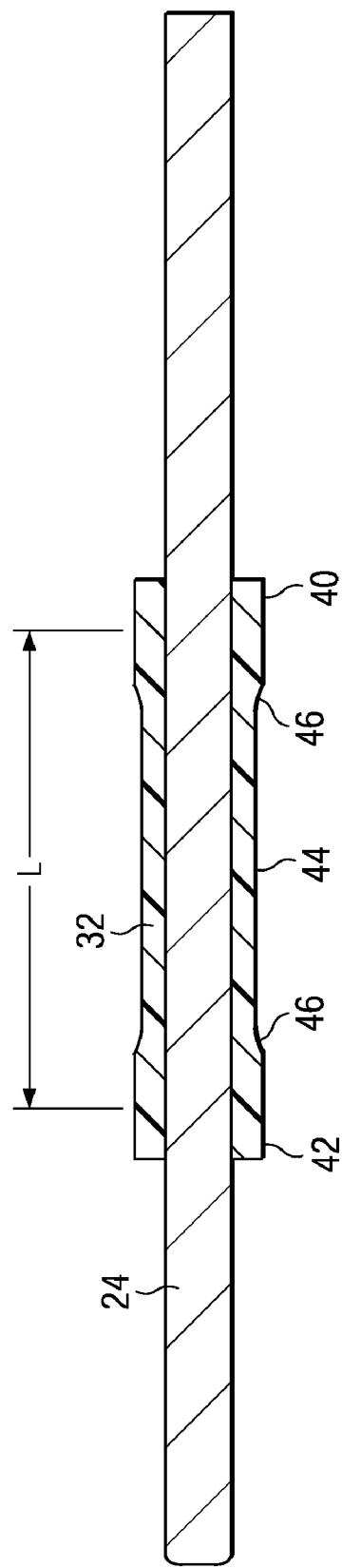
FIG. 5 is a cross-sectional view of a sheathed tether in accordance with and exemplary embodiment of the present invention.

The present disclosure relates generally to the field of orthopedic surgery, and more particularly to systems and methods for stabilizing a spinal joint or spinal motion segment. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Systems and devices for providing dynamic stabilization of one or more spinal motion segments are provided. The systems include a connecting element between two or more bone anchor assemblies that can be attached to two or more vertebral bodies of a spinal motion segment. The connecting element extends along a longitudinal axis and includes opposing end members with rod portions at each end engageable to respective ones of the anchor assemblies and a resilient intermediate element between the end members that allows movement of the vertebrae to which the connecting element is attached. The end members can be configured to interfit with the resilient intermediate element to provide a stabilization construct that is movable in response to movement of the spinal column. The resilient intermediate element, or bumper assembly, defines multiple planes and locations of motion relative to the longitudinal axis of the connecting element while providing appropriate stiffness and shear resistance for spinal stabilization as the spinal motion segment deviates from the neutral position.

The anchor assemblies discussed herein can be multi-axial or uni-axial in form, and can include an anchor member engageable to a vertebral body and a receiver, post or other device for receiving or engaging a respective end member of the connecting element. The multi-axial anchor assemblies allow the anchor member to be positioned at various angles relative to the connecting element engaging portion of the anchor assembly. The uni-axial anchor assemblies can also provide a fixed positioning of the connecting element engaging portion to the anchor member. The anchor member of the anchor assemblies can form a distal lower portion that is engageable to a vertebral body with the connecting element engaging portion positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The implant engaging portion can include a receiver with a U-shape, O-shape, or other shape that defines a passage that receives the respective end member of the connecting element therein, thereon, therethrough, or thereover, for example. The connecting element can extend from one or both of the anchor assemblies for securement to one or more additional vertebral bodies.

FIG. 1 illustrates an exemplary embodiment of an elongated connecting element 10 of the present invention. Connecting element 10 is configured to be attached or connected between two vertebrae to provide stabilization therebetween. The elongated connecting element 10 includes a first end member 12 configured to be connected to a first vertebra, a second end member 14 configured to be connected to a second vertebra, and a resilient intermediate element 16 positioned therebetween. The first end member 12 and the second end member 14 are preferably substantially aligned along a longitudinal axis A. Longitudinal axis A may have substantially zero curve or may have a non-zero curve, such as to facilitate insertion between bone anchor systems. Resilient intermediate element 16 extends along the longitudinal axis for a length L.

First end member 12 is provided with a first flange 18 and second end member 14 is provided with a second flange 20. Each of flange 18, 20 includes at least one opening 22. The resilient intermediate element 16 is disposed between the flanges 18, 20, and provides a shock absorbing effect in transmitting spinal column loads between the anchors to which it is engaged, particularly upon the application of a compressive longitudinal force, such as during spinal extension. Resilient intermediate element 16 can also permit relative movement between first and second end members 12, 14 to allow motion of the spinal column segment to which connecting element 10 is engaged.

In some embodiments, the flanges 18, 20 engage or abut the resilient intermediate element 16 in the neutral position of connecting element 10, due to the preload applied during assembly of element 10. The preload applied during assembly may vary, and in some embodiments, the flanges 18, 20 do not engage the resilient intermediate element 16 in the neutral position of connecting element 10, but will contact, or abut, the resilient intermediate element 16 upon the application of a longitudinal force to the connecting element 10. The first flange contacts or abuts the resilient intermediate element 16 at first abutment 21 and the second flange contacts or abuts the resilient intermediate element at second abutment 23, as illustrated in FIG. 2.

When the first end member 12 and the second end member 14 are moved toward each other, such as during extension of the spine when the connecting element 10 is attached along a spinal column, the flanges 18, 20 engage the resilient intermediate element 16 to apply or increase, depending on whether a preload force is already applied, a longitudinal force to the resilient intermediate member 16. The resilient intermediate member 16 then deforms and absorbs at least part of the applied force, and dampens the movement of the first end member 12 and the second end member 14 toward each other.

As illustrated in FIG. 2, a tether 24 passes through the resilient intermediate element 16 between first end member 12 and second end member 14. Tether 24 is disposed in a first bore 26, defined by first end member 12, and a second bore 28, defined by second end member 14. A stop member or ferrule 30 is secured to tether 24, for example by crimping, and limits the separation of the first end member 12 and the second end member 14, such as during flexion of the spine or due to preload. The first bore 26 and the second bore 28 are, for example, disposed axially along the longitudinal axis A.

FIG. 2 also illustrates a sheath 32 that at least partially surrounds the tether 24 that extends through a third bore 34 in the resilient intermediate element 16. As illustrated, the sheath 32 extends substantially continuously around the tether 24 for at least about length L. The sheath 32 encases the tether 24 for that portion of tether 24 surrounded by sheath 32, but also may have discontinuities, such as holes, slots, or the like, disposed along its length without departing from the spirit and scope of the invention. Sheath 32 may also have a helical shape, such as like a spring or a coil, that extends along its length and is wrapped, for example, around the tether 24. Sheath 32 may take any shape. The term "sheath" is merely illustrative and is not intended to be limiting. The sheath 32 may be of any design that partially or wholly encases, wraps, or is disposed along a portion of the length of the tether 24. As illustrated in FIG. 2, sheath 32 is thicker, with a greater outer diameter, radially inwardly of abutments 21, 23, and is thinner, with a lesser outer diameter through the remainder of the length L. The thinner diameter provides greater flexibility than a thicker diameter. The thicker end diameters provide greater resistance radially inwardly of the abutments 21, 23 to shear forces applied to the connecting element 10.

The first bore 26 and the second bore 28 are widened near the resilient intermediate element 16 to enable the sheath 32 to slide along the bore 26, 28 upon the application of a compressive longitudinal force to the connecting element 10, such as during spinal extension. When constructing the connecting element 10, it may be necessary to apply a compressive force along the longitudinal axis A to compress the intermediate resilient element 16 and expose part of the tether 24 for attachment of the stop member or ferrule 30. The increased diameter or widened portion of bore 28 enables the sheath 32 to travel along this widened portion of bore 28 to enable attachment of the stop member or ferrule 30 to the tether 24.

The increased diameter or widened portion of bore 28 also provides a seat 31 which the sheath 34 will contact upon application of significant longitudinal compressive force. In this way, the seat 31 of the bore 28 acts to limit the movement of first end member 12 with respect to second end member 14 to limit spinal extension when the connecting member 10 is attached to a spinal motion segment. The shape of the increased diameter portion of the bore 28 and of the face of seat 31 may be selected without departing from the spirit and scope of the invention. For example, the widened portion of bore 28 may be conical, frustroconical, pyramidal, hemispherical, or the like. And the seat 31 may be, for example, a cross section of any of these shapes or another shape altogether.

When a shear force is applied to the connecting element 10, it is possible that there would be radial displacement of first end member 12 with respect to second end member 14, and a portion of tether 24 may be displaced from the longitudinal axis A. For the purposes herein, a "shear" force is a force with a component vector that is perpendicular to the longitudinal axis A. The presence of the sheath 32 minimizes even the possibility that radial displacement of the first end member 12 with respect to the second end member 14 would have the effect that the tether 24 contacts and rubs against the interior of the first and/or second end member 12, 14 radially inwardly of first abutment 21 or second abutment 23 upon application of a shear force to the connecting member 10. In the event of radial displacement of the tether 24 by application of a shear force, the sheath 32 would contact the surface of the first bore 26 or the second bore 28 instead of the tether 24 itself contacting the surface.

FIG. 3 illustrates an embodiment in which the sheath 32 is discontinuous through length L and includes first collar 36 disposed in the first bore 26 radially inwardly from first abutment 21 and second collar 38 disposed in the second bore 28 radially inwardly from second abutment 23. In this embodiment, the sheath 32 does not extend substantially continuously along the third bore for the entire length L. The tether 24 is disposed through the first bore 26 and the second bore 28. Upon application of shear force to the elongated connecting element 10 substantial enough to deflect the tether 24, either the first collar 36 or the second collar 38 would contact the interior of the bore 26, 28 radially inwardly of the abutments 21, 23 before the tether 24 would contact the surfaces of the bores 26, 28.

FIG. 4 illustrates another view of the embodiment of connecting element 10 illustrated in FIG. 2, with the first end member 12, the second end member 14, and the resilient intermediate element 16.

Figure 6:
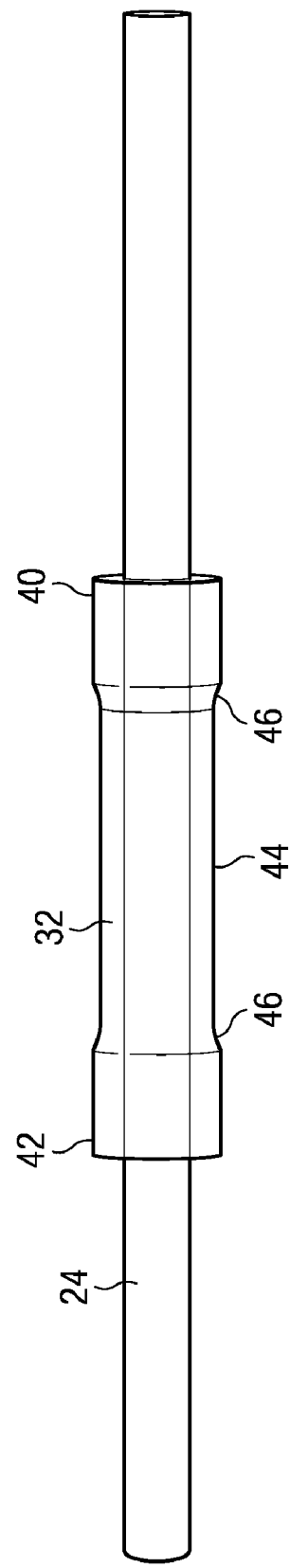
FIG. 6 is a phantom view of a sheathed tether in accordance with an exemplary embodiment of the present invention.

FIGS. 5 and 6 illustrate an embodiment of tether 24 with a sheath 32 that extends substantially along, or slightly greater than, length L. In this embodiment, the sheath 32 has a greater diameter at a first end 40 and a second end 42 than in the center 44, with transition sections 46 between the ends 40, 42 and the center 44 in which the diameter varies in a substantially linear transition. The shape of the sheath 32 may be selected based on the needs and requirements or each situation, and all such shapes are within the scope of the present invention. For example, the sheath 32 may be substantially cylindrical, prismatic, helical, and solid, perforated, striped, sliced, with any shape/pattern openings, apertures, or holes along all or part of its length, or the like. The sheath 32 also may be discontinuous with several different parts, such as the first collar 36 and the second collar 38, but is not limited to only a first and a second collar.

The form, shape, and the material of construction of the end members 12, 14, the resilient intermediate element 16, and the tether 18 can be selected based on criteria chosen by the user without departing from the spirit or scope of the invention. Some suitable materials are included in U.S. Ser. No. 11/028,999. For example, the tether may be flexible or non-flexible strands, wire, rope, cord, band, belt, suture, bar, cable, rod, mesh, fabric, or other suitable form and may be a metal cable, including a metal cable formed from metal strands, such as a cable of titanium, titanium alloys, cobalt chromium, cobalt chromium alloys, stainless steel, stainless steel alloys, or mixtures or alloys thereof. The end members 12, 14 also may be made of metal, such as titanium. Resilient intermediate element 16 may be of any shape, such as cylindrical or prismatic, including rectangular, pentagonal, hexagonal, etc., prisms, and may be made from various materials such as polyurethane or polycarbonate urethane, and may be made from a resorbable material. The resilient intermediate element 16 may be a single, unitary element or may be composed of more than one component element.

The sheath 32 may be made of a thermoplastic material, including polyetheretherketone (PEEK), carbon-reinforced PEEK, polyethylene terephthalate (PET), polyester, polyetherketoneketone (PEKK), polylactic acid materials (PLA and PLDLA), polyaryletherketone (PAEK), polysulfone, polyetherimide, polyimide; ultra-high molecular weight polyethylene (UHMWPE), cross-linked UHMWPE, polycarbonate, nano-material reinforced polymers, or mixtures or co-polymers thereof.

The sheath 32 may be affixed in any way without departing from the spirit and scope of the invention. An exemplary manner of fixation is overmolding the sheath 32 onto the tether 24. The sheath 32 may be fixed relative to the resilient intermediate element 16, in which case the tether 24 is slidably disposed within the sheath 32, or the sheath 32 may be fixed relative to the tether 24, in which case the sheath 32 is slidably disposed within the resilient intermediate element 16.

Figure 7:
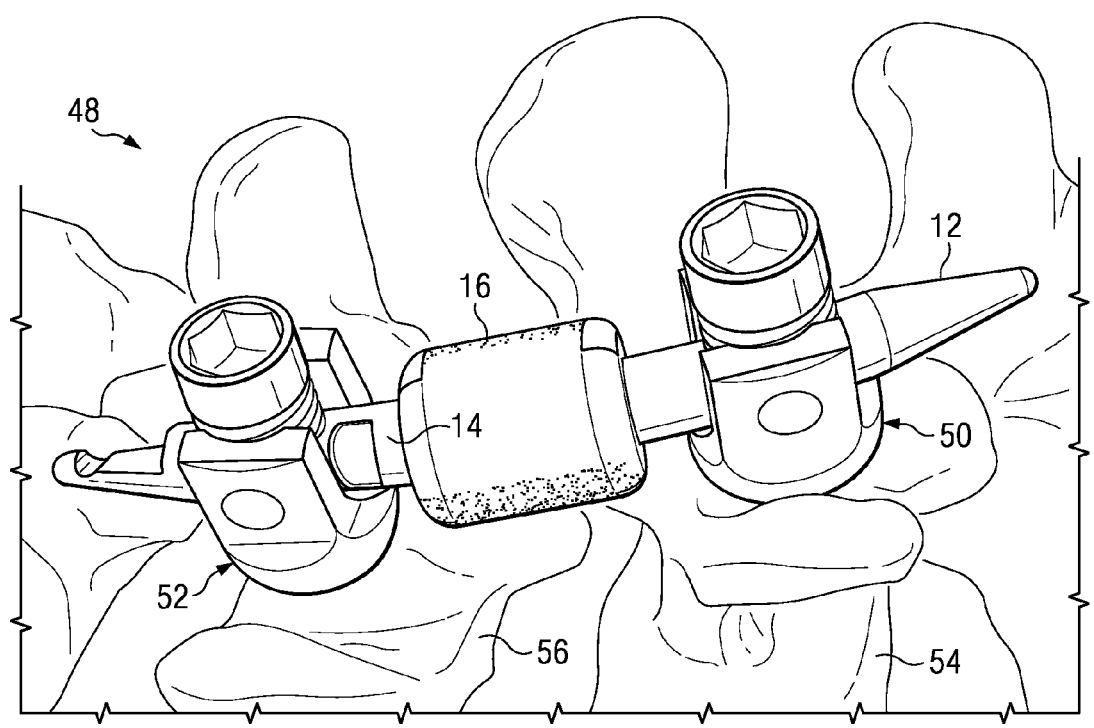
FIG. 7 is an exemplary embodiment of a system for spinal stabilization in accordance with the present invention.

FIG. 7 illustrates a system 48 for stabilizing a first vertebra or vertebral body with respect to a second vertebra or vertebral body in which a first bone anchor assembly 50 is attached to a first vertebra 54 and a second bone anchor assembly 52 is attached to a second vertebra 56. The stabilization system 48 is configured for attachment to a first vertebra 54 and a second vertebra 56, but it is to be noted that the invention includes such a system that is not attached to the first and second vertebra 54, 56. As described above, the bone anchor systems 50, 52 included herein can be multi-axial or uni-axial in form, and can include an anchor member attachable to a vertebral body and a receiver, post or other device for receiving or engaging a respective end member 12, 14 of the connecting element 10.

First end member 12 is configured to engage with first anchor system 50 and second end member 14 is configured to engage with second anchor system 52. In this way, the elongated connecting element 10 is configured to be attached to and to stabilize a first vertebra 54 and a second vertebra 56.

Figure 8:
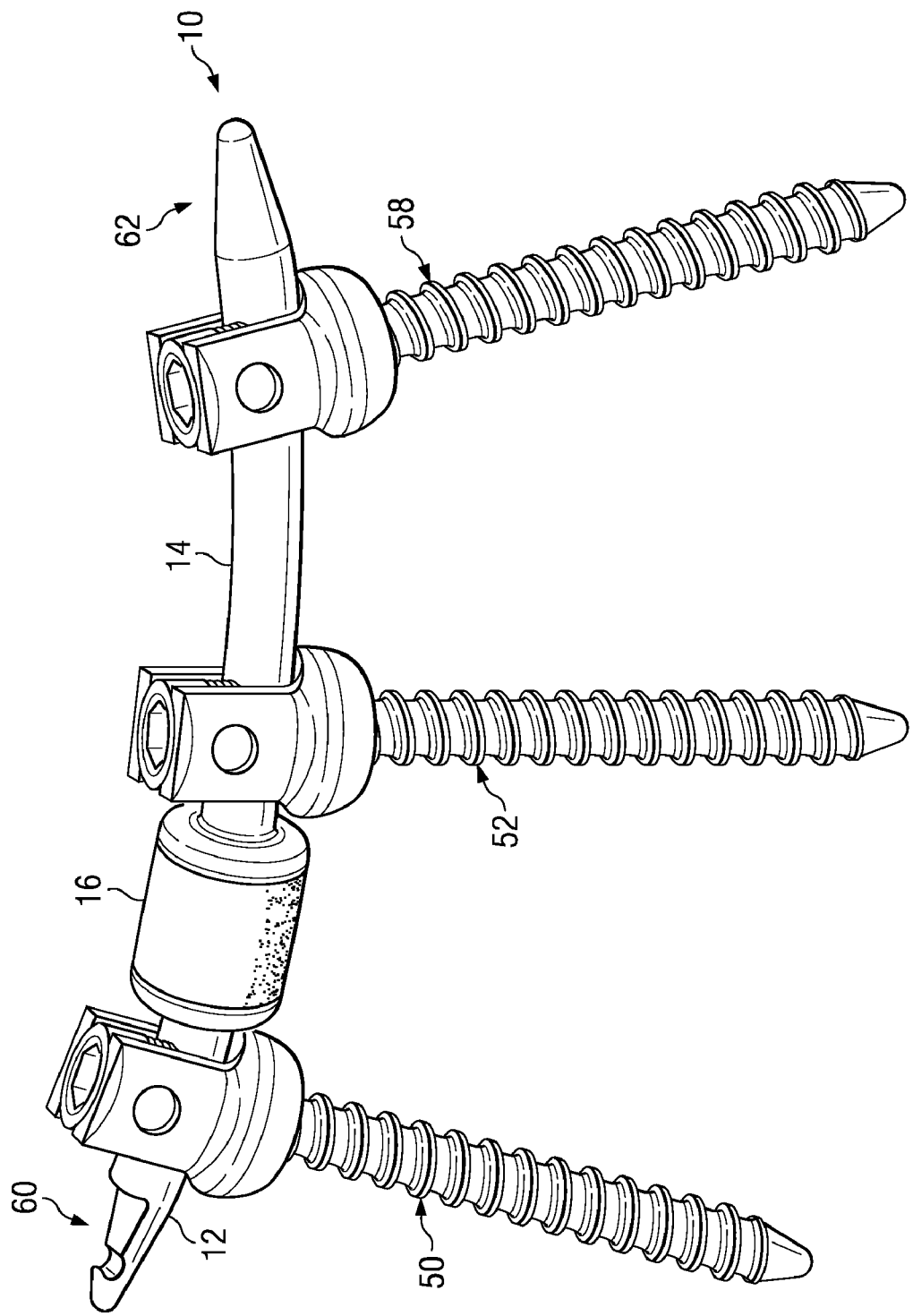
FIG. 8 is an exemplary embodiment of a system for spinal stabilization in accordance with the present invention.

FIG. 8 illustrates an embodiment of the stabilization system 48 having a third anchor system 58 that can be used to anchor to a third vertebra or vertebral body. In this embodiment, the second end member 14 is elongated and is anchored to both the second anchor system 52 and the third anchor system 58. This provides for stabilization of three adjacent vertebrae. The system 48 may also stabilize three adjacent vertebra without having the second anchor assembly 52, in which case the connecting element 10 will be engaged between non-adjacent vertebrae to which the first anchor system 50 and the third anchor system 58 are attached. In this manner, the connecting member 10 may be used to stabilize any number of vertebral bodies by attachment to adjacent or non-adjacent vertebrae.

The first end 12 or the second end 14 may be provided with a notched area 60, for example for engagement with an inserter, or a tapered area 62 to facilitate placement of the connecting element 10.

In yet another embodiment, the elongated connecting member 10 may include a second resilient intermediate member 16 disposed between the second anchor assembly 52 and the third anchor assembly 58. In this manner, there may be any number of resilient intermediate elements 16 between any number of adjacent or non-adjacent vertebrae.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

We claim:

1. An elongated connecting element for stabilizing a first vertebra with respect to a second vertebra, the elongated connecting element comprising:
   a. a first end member and a second end member substantially aligned along a longitudinal axis;
   b. a resilient intermediate element positioned between the first end member and the second end member, the resilient member having a length L;
   c. a tether extending between the first end member and the second end member and through the resilient intermediate element; and
   d. a sheath at least partially surrounding the tether along a portion of the length of the tether, the sheath extending through the resilient intermediate member and along the longitudinal axis outward beyond the resilient intermediate member.

2. The elongated connecting element of claim 1, wherein the longitudinal axis is curved.

3. The elongated connecting element of claim 1, wherein the resilient intermediate element abuts the first end member at a first abutment and abuts the second end member at a second abutment.

4. The elongated connecting element of claim 3, wherein the sheath at least partially surrounds the tether radially inwardly from the first abutment or radially inwardly from the second abutment.

5. The elongated connecting element of claim 3, wherein the sheath is discontinuous and comprises at least one first collar disposed in a bore within the first end member radially inwardly from the first abutment and at least one second collar disposed in a bore within the second end member radially inwardly from the second abutment.

6. The elongated connecting element of claim 1, wherein the sheath at least partially surrounds the tether substantially continuously along the entire length L.

7. The elongated connecting element of claim 1, wherein the sheath comprises a thermoplastic material.

8. The elongated connecting element of claim 7, wherein the thermoplastic material is selected from the group consisting of polyetheretherketone (PEEK), carbon-reinforced PEEK, polyethylene terephthalate (PET), polyester, polyetherketoneketone (PEKK), polylactic acid materials (PLA and PLDLA), polyaryletherketone (PAEK), polysulfone, polyetherimide, polyimide; ultra-high molecular weight polyethylene (UHMWPE), cross-linked UHMWPE, polycarbonate, and nano-material reinforced polymers.

9. The elongated connecting element of claim 1, wherein the sheath is overmolded onto the tether.

10. The elongated connecting element of claim 1, wherein the sheath is fixed relative to the resilient intermediate element and the tether is slideably disposed within the sheath.

11. The elongated connecting element of claim 1, wherein the sheath is fixed relative to the tether and is slideably disposed within the resilient intermediate element.

12. The elongated connecting element of claim 1, wherein the tether is flexible.

13. The elongated connecting element of claim 12, wherein the tether comprises metal strands, the metal selected from the group consisting of titanium, titanium alloys, cobalt chromium, cobalt chromium alloys, stainless steel, and stainless steel alloys.

14. The elongated connecting element of claim 1, wherein the tether is not flexible.

15. An elongated connecting element for stabilizing a first vertebra with respect to a second vertebra, the elongated connecting element comprising:
   a. a first end member having a bore with an inner surface and a second end member having a bore with an inner surface, the first and second end members substantially aligned along a longitudinal axis;
   b. a resilient intermediate element positioned between and abutting the first end member and the second end member, the resilient member having a length L;
   c. a tether extending between the first end member and the second end member and through the resilient intermediate element; and
   d. means to prevent the tether from contacting the inner surface of the first end member radially inwardly from the abutment of the resilient intermediate element and the first end member and to prevent the tether from contacting the inner surface of the second end member radially inwardly from the abutment of the resilient intermediate element and the second end member.

16. The elongated connecting element of claim 15, wherein the means to prevent the tether from contacting the first and the second end members comprises a sheath disposed at least partially around the tether along a portion of the length of the tether corresponding to length L.

17. The elongated connecting element of claim 15, wherein the means to prevent the tether from contacting the first and the second end member comprises at least one first collar disposed within a bore within the first end member radially inwardly from the abutment of the first end member with the resilient intermediate element and at least one second collar disposed within a bore within the second end member radially inwardly from the abutment of the second end member with the resilient intermediate element.

18. The elongated connecting element of claim 17, wherein the tether is disposed within the at least one first collar and the at least one second collar.

19. A spinal stabilization system, comprising:
  a. at least a first bone anchor system connectable to a first vertebra and a second bone anchor system connectable to a second vertebra;
  b. a flexible elongated connecting element configured to extend between the first bone anchor system and the second bone anchor system;
  wherein the flexible elongated connecting element comprises a sheathed tether extending through a resilient intermediate member disposed such that the resilient intermediate member is arranged between the first bone anchor system and the second bone anchor system when the flexible elongated connecting element is connected thereto;
  the sheathed tether having a length and including a variable outer diameter along the length.

20. The spinal stabilization system of claim 19, wherein the length of the sheathed tether is greater than the resilient intermediate member.

* * * * *